US00PP10313P

United States Patent [19]

Guillou et al.

[11] Patent Number: Plant 10,313

[45] Date of Patent: Mar. 31, 1998

[54] GERANIUM NAMED 'GUICHARA'

[75] Inventors: Bernard Guillou; Jacques Guillou; Maurice Guillou, all of Saint-Malo, France

[73] Assignee: Fleur License Service, Ad Bemmel, Netherlands

[21] Appl. No.: 723,803

[22] Filed: Sep. 30, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Assistant Examiner*—Melissa L. Kimball

*Attorney, Agent, or Firm*—Foley & Lardner

[57] ABSTRACT

A new geranium plant named 'Guichara', characterized by double-type flowers with 16–22 petals per flower which are mauve-violet in color; a corolla with a diameter of approximately 50 mm; early flowering which is luxuriant in the summer; plant habit that exhibits branching with good ramification and internode length of approximately 40 to 50 mm; plant height of approximately 30 to 35 cm; ivy-shaped foliage with a diameter of approximately 80 to 100 mm and foliage that lacks variegation but exhibits brown zonation and slightly jagged edges.

3 Drawing Sheets

The present invention comprises a new and distinct cultivar of geranium, botanically known as *Pelargonium peltatum l'Hér. ex Ait*, and hereinafter referred to by the cultivar name 'Guichara'. 'Guichara' is a product of planned breeding program which had the objective of creating new geranium varieties cultivars with a mauve-violet flower color and compact and well-branched plant habit.

It is anticipated that this plant will be domestically marketed under the synonym 'Charade'.

'Guichara' was originated from a hybridization made in a controlled breeding program in Saint Malo, Bretagne, France in 1991. The male and female parents were 'Roasias' and 'Améthiste', respectively, from the proprietary Guillou collection. Both parents have mauve violet flower color and double-type flowers.

'Guichara' was discovered and selected as one flowering plant within the progeny of the stated cross by the inventors in 1991 in a controlled environment in Saint Malo, France.

The first act of asexual reproduction, of 'Guichara' was accomplished when vegetative cuttings were taken from the initial selection in 1994 in a controlled environment in Haalderen, The Netherlands, by a technician working under the supervision of the inventors. Horticultural examination of selected units initiated in 1994 has demonstrated that the combination of characteristics as herein disclosed for 'Guichara' are firmly fixed and are retained through successive generations of asexual reproduction.

'Guichara' has not been observed under all possible environmental conditions. The phenotype may vary with variations in environment such as temperature, light intensity, and daylength, without any change in genotype. The following observations, measurements, and comparisons describe plants grown in Haalderen, The Netherlands, under greenhouse conditions which approximate those generally used in commercial practice.

The following traits have been repeatedly observed to be basic characteristics of 'Guichara' which in combination distinguish this geranium as a new and distinct cultivar:

1. Mauve violet double-type flowers.
2. Green foliage with slightly serrated edges.
3. Early-flowering which is luxuriant in summer.
4. Regular flowers displayed on attractive foliage.

Of the many commercial cultivars known to the present inventors, 'Guichara' most closely resembles 'Rodhaman'. Unlike 'Rodhaman', however, 'Guichara' is resistant to oedema. 'Guichara' grows more vigorously than the parent 'Améthiste' and flowering is earlier and more abundant. 'Guichara' roots more quickly than either parent.

The accompanying photographic drawings show typical flower and foliage characteristics of 'Guichara'.

Sheet 1 is a side view of a plant showing open and closed flowers.

Sheet 2 is a top and bottom view of an individual flower from the cultivar.

Sheet 3 is a top and bottom view of an individual leaf from 'Guichara'.

In the following description, color references are made to The Royal Horticultural Society (R.H.S.) Colour Chart. The color values were determined indoors in 1996 under greenhouse conditions at Haalderen, The Netherlands. Colors are as true as possible with illustrations of this type.

Classification:

*Botanical.*—*Pelargonium peltatum l'Hér. ex Ait.* cv. 'Guichara'.

*Commercial.*—Ivy geranium 'Charade'.

Inflorescence

A. Umbel:
- *Average diameter.*—60–80 mm.
- *Average depth.*—35 mm.
- *Pedicel length.*—70–120 mm in greenhouse.

B. Corolla:
- *Average diameter.*—50 mm.
- *Form.*—Double-type.
- *Number of petals.*—16–22.
- *Color (generally tonality from a distance of three meters).*—Mauve violet.
- *Color (abaxial).*—Approx. R.H.S. 81b.
- *Color (adaxial).*—Approx. R.H.S. 81c.

C. Bud:
- *Shape.*—10 mm.
- *Color (abaxial).*—Approx. R.H.S. 81B.
- *Color (adaxial).*—Approx. R.H.S. 81B.

D. Reproductive organs:
- *Androecium.*—not strong/not copious.
- *Gynoecium.*—Strongly developed.

E. Spring flowering response period: 8–6 flowers opened 15 weeks after planting of unrooted cuttings (pinched plants).

F. Outdoor flower production: abundant in summer producing about 15 flowers per peduncle.

G. Durability: Shatter resistance medium.

Plant

A. Foliage:
*Form.*—Ivy-shaped.
*Margin.*—Slightly jagged; diameter 80–100 mm.
*Color* (*abaxial*).—Slightly dark green.
*Color* (*adaxial*).—Slightly dark green.
*Color* (*zonation*).—Brown.
*Variegation.*—None.
*Margin.*—Green.

B. General appearance and form:
*Internode length.*—40–50 mm.
*Branching pattern.*—Good ramification.
*Height.*—30–35 cm.

C. Tolerance to botrytis: Good resistance.

We claim:

1. A new and distinct cultivar of geranium plant named 'Guichara', as illustrated and described.

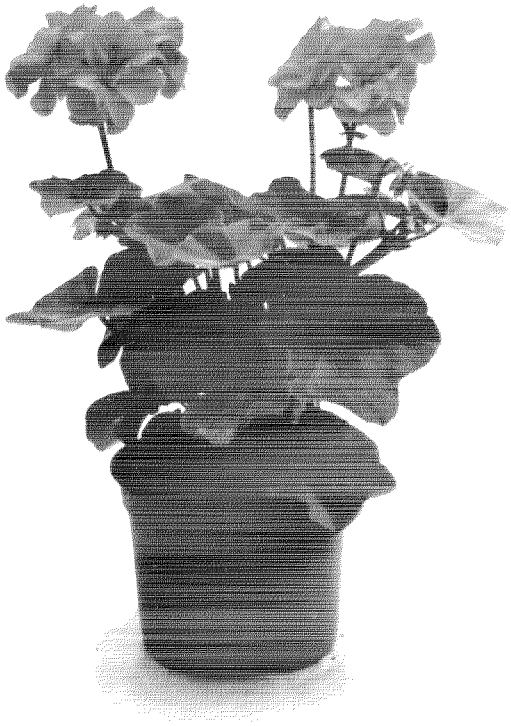

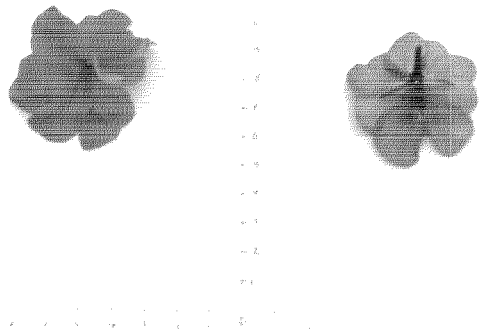

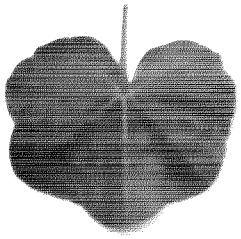
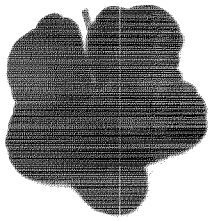

* * * * *